United States Patent
Hsieh

(10) Patent No.: US 8,802,732 B2
(45) Date of Patent: Aug. 12, 2014

(54) LYCOPENE AND RESVERATROL COMPOSITIONS FOR NK CELL ACTIVATION RESULTING IN ANTI-NEOPLASTIC EFFECT

(75) Inventor: Kun Lung Hsieh, Ho Chi Minh (VN)

(73) Assignee: Hsiehs Biotech (Singapore) Pte Ltd, Singapore (SG)

( * ) Notice: Subject to any disclaimer, the term of this patent is extended or adjusted under 35 U.S.C. 154(b) by 0 days.

(21) Appl. No.: 13/320,480

(22) PCT Filed: Apr. 13, 2010

(86) PCT No.: PCT/SG2010/000147
§ 371 (c)(1), (2), (4) Date: Jan. 30, 2012

(87) PCT Pub. No.: WO2010/132024
PCT Pub. Date: Nov. 18, 2010

(65) Prior Publication Data
US 2012/0136061 A1    May 31, 2012

(30) Foreign Application Priority Data

May 14, 2009 (SG) ............................... 200903301-0
Jan. 27, 2010 (SG) ............................... 201000589-0

(51) Int. Cl.
*A61K 31/185* (2006.01)
*A61K 31/07* (2006.01)

(52) U.S. Cl.
USPC ........................................ 514/576; 514/725

(58) Field of Classification Search
USPC ................................................ 514/576, 725
See application file for complete search history.

(56) References Cited

U.S. PATENT DOCUMENTS

2008/0248129 A1   10/2008   Bartunek et al.

FOREIGN PATENT DOCUMENTS

| CN | 1439377 A | * | 9/2003 |
| WO | 03068202 A1 | | 8/2003 |
| WO | WO 03068202 A1 | * | 8/2003 |

OTHER PUBLICATIONS

CN 1439377 A, Lui: English abstract (2003).*
Cheng et al., "Structure-activity relationship studies of resveratrol and its analogues by the reaction kinectics of low density lipoprotein peroxidation," Bioorganic Chemistry, 34, 2006, 142-157.
Naviglio et al., "Characterization of High Purity Lycopene from Tomato Wastes Using a New Pressurized Extraction Approach," Journal of Agricultural and Food Chemistry, 2008, 56, 6227-6231.
Wu et al., "Preparation, physicochemical characterization, and antioxidant effects of quercetin nanoparticles," International Journal of Pharmaceuticals, 346, 2008, 160-168.

* cited by examiner

*Primary Examiner* — Kevin E Weddington
(74) *Attorney, Agent, or Firm* — Gregory P. Eichorn

(57) ABSTRACT

A carotenoid and a terpenoid in therapeutically-effective amounts is disclosed such that, upon ingestion in one preparation, or in two separated preparations, simultaneous or sequentially, and upon metabolism, the activity of natural killer (NK) cells is elevated. Specifically, the composition comprises lycopene and resveratrol in the range of 1:10 to 10:1 by molar; more preferably 1:1 to 3:1 by molar, and most preferably at 3:1. Alternatively, the preferred ratio may be expressed as 1:4 to 25:1 by weight; more preferably 2½:1 to 7½:1 by weight, and most preferably at 7½:1. The composition may be formulated for oral intake as a pharmaceutical, dietary supplement or food product and provided in therapeutically effective amounts to a mammal, preferably in a dosage of about 3.5 mg per day per 20 g of a mammalian body mass in a ratio of 2½:1 by weight, which can be translated to about 400 mg to 1000 mg per day for a typical human in need of elevating NK cell activity. Preferably, the therapeutically-effective aspect of the composition includes its metabolically-producing agents, prodrugs, metabolites or intermediate compounds useful in triggering NK cells into cytotoxic or cytolytic response.

19 Claims, 8 Drawing Sheets

LYCOPENE AND RESVERATROL COMPOSITIONS FOR NK CELL ACTIVATION RESULTING IN ANTI-NEOPLASTIC EFFECT

CROSS-REFERENCE TO RELATED APPLICATIONS

This United States utility patent application is the §371 national phase of PCT international patent application no PCT/SG2010/000147, having an international filing date of Apr. 13, 2010, which claims benefit of priority to Singapore Patent Applications Serial Nos. SG 2010 00589 0, filed Jan. 27, 2009; and SG 2009 03301 0, filed May 14, 2009. The aforementioned applications are expressly incorporated herein by reference in their entirety and for all purposes.

TECHNICAL FIELD

A composition of phytochemicals comprising a carotenoid and a terpenoid is disclosed. Specifically, the carotenoid is lycopene and the terpenoid is resveratrol and both compounds are admixed in proportion that, upon metabolism in a mammal body, is found to be synergistic in potentializing immunity especially via NK cell activation leading to anti-neoplastic mechanism of the body.

BACKGROUND ART

In our co-pending patent application No. SG 200903301-0 filed on 14 May 2009 the priority of which is hereby claimed, we disclosed a novel composition comprising lycopene and resveratrol in certain ratios or proportions that have shown synergistic effect in inhibiting cancerous growths in mammals. The specific anti-neoplastic mechanism aided by our compositions was then unknown.

A mammalian body's innate immune response is provided by NK cells which are large granular lymphocytes (LGLs) providing immuno-surveillance of any cells of the body turning cancerous or that has been infected by a pathogen, or a foreign body, e.g. transplanted tissue. As first line innate defence, NK cells do not require antigen-dependent activation. Its immunosurveillance function works by seeking out cells distressed by pathogen infection or had turned cancerous, and killing these cells by cytotoxic or cytolytic means, i.e. by releasing cytoplasmic protein granules such as perforin and granzyme that are cytotoxic to the target cells causing them to die by apoptosis such as cytolysis.

Given their strong cytolytic activity and potential auto-activity, NK cell activity is tightly regulated wherein it must receive a triggering biochemical signal in order to be activated. The biochemical trigger includes double-stranded RNA, cytokines, Fc receptor and other applicable ligand receptors. Tumour risk is thus taken to be inversely related to NK cell population level or activity.

Prior art known to us that attempted to activates NK cell activity via biochemical signalling are as follows. U.S. Pat. No. 4,883,662 (Stout) discloses the use of a biologic to boost the population of NK cells in patients suffering from cancer. The biologics are produced by introducing a strain of immunosuppressive virus into an animal, thereby stimulating the animal to produce the desired biologics which may be harvested and fractionated or purified for administration into the blood stream of cancer patients by injection.

U.S. Pat. No. 5,728,378 (Hellstrand) details a combination of cytokine, interferon-α and a composition containing histamine and serotonin as a pharmaceutical preparation to increase the activity of NK cells in the presence of monocytes. The preparation is administered by local or systemic injection or infusion into the bloodstream of the patients suffering from cancer or viral-infections. The preparation acts synergistically in elevating the activity of NK cells wherein the composition containing histamine and serotonin functions in suppressing monocytes activities therefore enabling the activation of NK cells by interferon-α.

In a subsequent U.S. Pat. No. 6,063,373 (Hellstrand), a combination consisting NK cells activators and an intracellular hydrogen peroxide inhibitor is employed for enhancing NK cells activities in the presence of monocytes. The NK cell activators are selected from the group of cytokines comprising Interleukin-1 (IL-1), Interleukin-2 (IL-2), Interleukin-12 (IL-12), Interleukin-15 (IL-15), Interferon-α (IFN-α), Interferon-β (IFN-β), or Interferon-γ (IFN-γ). The activators may also be in the form of flavonoids selected from the group consisting flavone-8 acetic acid (FAA) and xanthenone-4 acetic acid (XAA). Meanwhile the intracellular hydrogen inhibitors are selected from histamine, hydrogen receptor agonist and serotonin.

Not many disclosures relating to plant-based dietary compositions that might be enhancing NK cell activity—either by way of NK cell proliferation or elevating their activity—for purposes of effective therapeutic treatment for tumours and infections have been found. In European Patent EP-1,243,274 (Lu Kung-Ming) it is suggested that aqueous soy extract fermented by a particular bacteria strain of the genus *Lactobacillus* or optionally by a *Saccharomyces cerevisiae* yeast would induce cell apoptosis. In United States Patent Publication US 2002/010149 (Yagita), it is described that the mycelia of *Lentinus edodes* (also known as shiitake) may induce IL-12 production which activates NK cells. In PCT patent publication No. WO 2007/131767 (Goral-Czyk) a combination of lycopene and genistein for therapy of prostate carcinoma wherein one of the embodiments may optionally include resveratrol without suggesting affect on NK cell activity.

SUMMARY OF DISCLOSURE

It now appears from our further and continuing research that the anti-neoplastic mechanism benefited from the consumption and metabolism of certain phytochemicals with the elevation of NK cells' immuno-surveillance activity. Our phytochemical composition is found to significantly elevate NK cell number and its activity in mammals. In this specification, the term "elevation of NK cell activity" is the mixed effect of NK cell proliferation and increased cytolytic capacity. In particular, a significant synergistic effect is found in combining 2 specific phytochemicals compare to any one of them alone.

Broadly speaking, our composition comprises a carotenoid and a terpenoid in therapeutically-effective amounts such that, upon ingestion and metabolism, the activity of large granular lymphocytes (LGL), including natural killer (NK) cells is elevated. Specifically, the composition comprises lycopene and resveratrol in therapeutically-effective amounts for elevating activity of NK cells.

In one aspect of the invention, the composition comprises lycopene and resveratrol according to claim 2 wherein the elevated NK cell activity includes increased proportion of NK cells among total lymphocytes. The NK cell activity elevation includes providing biochemical signal triggering NK cells into cytotoxic or cytolytic response. Alternatively, the elevated NK cell activity includes increasing the response potential of individual NK cells which biochemical signal triggering optionally includes any one or combination of double-stranded RNA, cytokines, Fc receptor and other applicable ligand receptors. The elevated NK cell's cytotoxicity may be prolonged.

In a second aspect of the invention, a preferred ratio of lycopene:resveratrol is in the range of 1:10 to 10:1 by molar; more preferably 1:1 to 3:1 by molar, and most preferably at 3:1. Alternatively, the preferred ratio may be expressed as 1:4 to 25:1 by weight; more preferably 2½:1 to 7½:1 by weight, and most preferably at 7½:1. The composition may be formulated as a pharmaceutical, dietary supplement or food product and provided in therapeutically effective amounts to a mammal, preferably in a dosage of about 3.5 mg per day per 20 g of a mammalian body mass in a w/w ratio of lycopene to resveratrol=2½:1, which can be translated to about 400 mg to 1000 mg per day for a typical human in need of elevating NK cell activity.

In a third aspect of the invention, the lycopene and resveratrol composition is preferably formulated for oral intake. Alternatively, it may be delivered or provided for intake sequentially. Preferably, the therapeutically-effective aspect of the composition includes its metabolically-producing agents, prodrugs, metabolites or intermediate compounds useful in triggering NK cells into cytotoxic or cytolytic response.

LIST OF ACCOMPANYING DRAWINGS

Accompanying this specification are drawings which may provide a better understanding of our invention in conjunction with the detailed description that follows. The drawings, which are listed below, are intended to provide exemplary and non-limiting embodiments of our invention, in which.

DETAILED DESCRIPTION OF SPECIFIC EMBODIMENTS

Figure 1:
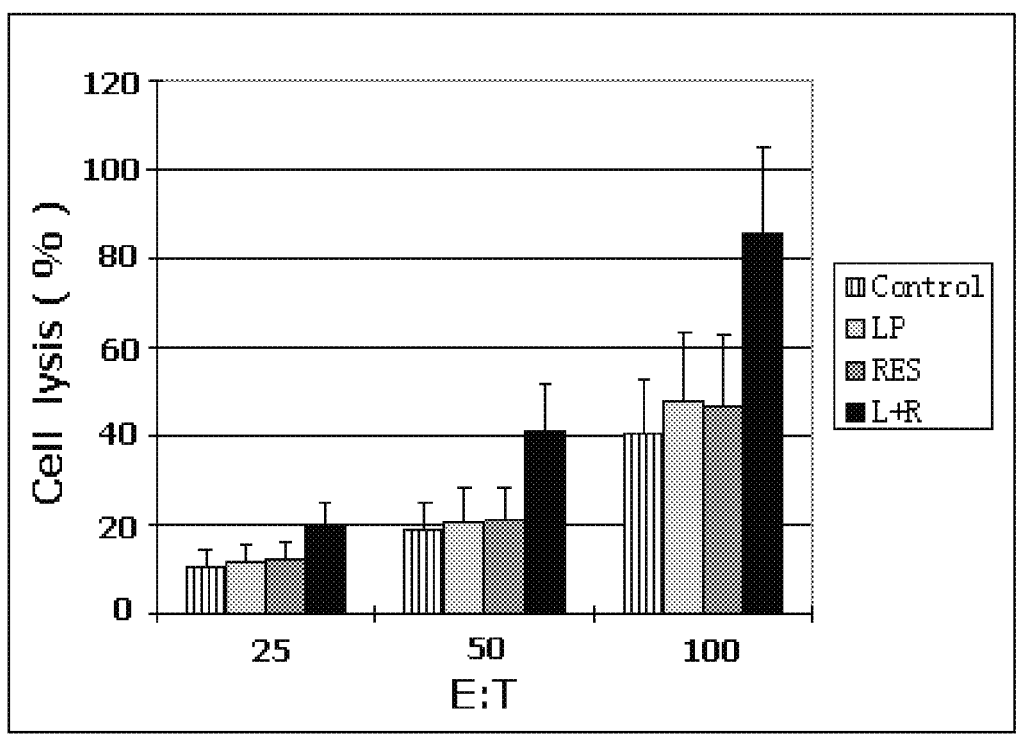
FIG. 1 shows a bar graph showing the NK cells toxicity in groups of mice with different treatment including control, lycopene only, resveratrol only and combination of lycopene and resveratrol.

Whereas we have broadly defined our composition as comprising a carotenoid and a terpenoid in therapeutically-effective amounts such that, upon ingestion and metabolism, the activity of large granular lumphocytes (LGL), including natural killer (NK) cells is elevated, as a specific embodiment of the composition, the carotenoid is lycopene while the terpenoid is resveratrol.

Lycopene

Lycopene is one of the six carotenoids which can be ingested by and accumulate in human body [Ref. 1: Mein (2008)]. It is mainly distribute in testis, prostate, liver and intestines. Lycopene is the most potent anti-oxidant on earth, exhibiting 3.2- and 100-folds higher anti-oxidative activity than β-carotene and vitamin E respectively.

Previous studies have revealed a number of health-promoting functions of lycopene including anti-ageing, enhancing immunity, reducing risk of cardiovascular diseases and incidence of malignancies, especially oral, throat, gastric, colon and uterus carcinomas. Clinical trials show that lycopene is effective in suppressing tumor growth and metastasis, especially for pancreatic, lung and gastric carcinomas [Ref. 2: Giovannucci (1999); Ref. 3: Gann (1999)]. Because of its multiple beneficial effects, lycopene is now recognized as a star healthy food supplement in the $21^{st}$ century and is gaining popularity world-wide. In developed countries including the U.S., Western Europe, Japan and Israel, huge costs and efforts have been and are continued to be spent in related research and development of lycopene-containing drugs, food supplements, foods and cosmetics.

In human intestine, lycopene forms micelles with fat and bile acids. These micelles can be observed at intestinal mucosal cells. Natural lycopene occur in all-trans form. Gastric acid can convert all-trans lycopene into various cis-isomers, which are believed to exhibit higher bioavailability. A total of 15-18 isomers have been found in human body, possibly corresponding to the wide variety of physiological functions of lycopene. The anti-oxidative activity alone, however, does not explain the anti-neoplastic and cardiovascular disease-preventing effects of lycopene. Recently, it has been hypothesized that lycopenoids may regulate gene expression in a manner similar to vitamin A. Known lycopenoids including 5,6-dihydroxy-5',6'-dihydrolycopene, 2,6-cyclolycopene-1,5-diol A & B, apo-10'-lycopenoic acid, acycloretinoic acid, apo-8'-lycopenal, apo-10'-lycopenal, apo-12'-lycopenal and apo-14' lycopenal. [Ref. 4: Ruhl (2004); Ref. 5: Lindshield, (2007); Ref. 1: Mein (2008)].

For in vitro and in vivo experiments, effect of lycopene is observed at much higher concentration than that in human body, suggesting possible co-factors. In 2008, the first reports came in to describe the necessity of co-factors for optimal anti-neoplastic effect of lycopene. [Ref. 6: Mossine (2008); Ref. 7: Venkateswaran (2009)].

Resveratrol

Resveratrol is a terpenoid found abundantly in grape skin, peanut, pineapple and knotweed rhizome. Resveratrol is an antioxidant and decreases blood viscosity, suppresses platelet coagulation, enhances vasodilation and thus generally promotes blood circulation. Resveratrol has hypolipidemic feature [Ref. 8: Arichi (1982)] and thus plays an important role in preventing atherosclerosis and ischemic heart diseases. Resveratrol is also known to have antineoplastic effect and is a natural substitute of estrogen. Further functions of resveratrol include anti-ageing effect, preventing oxidation of low-density lipoprotein (LDL) cholesterol, anti-inflammation and anti-allergic effect. Other uses of resveratrol include therapy of acute infectious hepatitis, menostasis, rheumatism, bone and muscle pain, bronchitis, cholecystolithiasis, hypercholesterol and hypertriglyceride condition.

Resveratrol is also known to regulate the immune system [Ref. 9: Kimura (1985); Ref. 10: Gao (2001)]. It inhibits synthesis and release of pro-inflammatory mediators, inhibits enzymes such as cyclooxygenase-1 or cyclooxygenase-2, suppresses lymphocyte proliferation, enhances activation of cytotoxic T-cells, and stimulates secretion of cellular factors.

Most importantly, resveratrol can inhibit the activity of transcriptional factor such as *Nuclear Factor-kappa light chain enhancer of activated B cells* (NF-κB), and thus may possess anti-neoplastic effect via regulating human immunity [Ref. 11: Tsai (1999); Ref. 12: Falchetti (2001); Ref. 13: Heynekamp (2006)].

Even upon ingestion of large amounts of resveratrol, its intact form presents only in trace amounts in the human body [Ref. 14: Andlauer (2000); Ref. 15: De Santi (2000)] and is far below that which can kill tumor cells in vitro. However, the anti-neoplastic effect of resveratrol is evident in a number of in vivo experiments [Ref. 16: Vitrac X (2003)]. These findings suggest that the anti-neoplastic effect of resveratrol is via some of its metabolites in human body or mice. We have conducted a number of experiments which protocol and results are described in the following.

Protocol

Isolation of NK Cells:

NK cells were isolated from Balb/c mice spleen. Each group of mice were killed at day 7 post-feeding of lycopene/resveratrol. The spleens were excised and soaked in 75% ethanol for 5 min, and smeared gently on cell sieves. The single cells were collected by flushing the sieve with RPMI-1640 medium. The derived total spleen cells were isolated by centrifugation at 2000 rpm by placing the mixture on the top of lymphocyte separation solution for 25 min. The white-colored lymphocyte layer was recovered carefully, and washed twice with serum-free RPMI-1640 medium, counted and transferred into 6-well plates as the stock. The lymphocytes thus prepared contains 10-20% of NK cells, and used for NK cell assay [Ref. 18: Zhang (2006)].

Isolation of B16 Melanoma Cells:

The B16 melanoma was excised from a tumor-bearing C57 mouse, and soaked in Hank's medium for 30 min. The adipose and necrotic parts of the tumor were removed, and the tumor was cut into small pieces and treated with RPMI-1640 containing 0.1% type II collagen at 4° C. for 12 h. The digested tumor tissue was gently passed through 100-mesh cell sieve and 100% Ficoll was used to separate tumor cells by centrifugation.

Measurement of Cytotoxic Activity of NK Cells:

NK cells isolated from mice spleen were mixed with B16 melanoma cells at ratios of 25:1, 50:1 and 100:1, and incubated at 37° C. After 5 h, the lactate dehydrogenase (LDH) activities in 100 μl of culture media were measured as the cytolytic activity of NK cells. Cytotoxicity is calculated according to the following formula.

$$\text{Cytotoxicity} = \left[\frac{(OD_{experiment} - OD_{effector\ spontaneous} - OD_{target\ spontaneous})}{(OD_{target\ maximum} - OD_{target\ spontaneous})}\right] \times 100\%$$

wherein $OD_{experiment}$: the optical density value derived from medium of target cell and NK cell co-culture;

$OD_{effector\ spontaneous}$: the optical density value derived from NK cell medium;

$OD_{target\ spontaneous}$: the optical density value derived from target cell medium;

$OD_{maximaum}$: the optical density value derived from 100% lysis of target cell by 1% NP40.

EXAMPLE 1

In this experiment, mice were divided into four groups (6 mice in each group): (1) control group, (2) test group for lycopene (2 mg/day) treatment, (3) test group for resveratrol (4 mg/day) treatment and (4) test group for Golden Lypres (6 mg/day) treatment. Golden Lypres is a registered product of the Hsiehs Biotech composed of lycopene and resveratrol in a ratio of 1:2 in w/w. The test groups were orally administrated daily for one week and the NK cytotoxic activities (cytotoxicity) were measured according to the standard protocol described above. The NK cytotoxicities of groups administrated with either lycopene or resveratrol, only showed a slight increase (not significantly). Whereas the group administrated with Golden Lypres™ gained >100% elevation of the NK cell cytotoxicity (P<0.01).

The effect of lycopene and resveratrol on NK cell activity elevation is plotted as a bar graph in FIG. 1. The increase of NK cytotoxicity is a result of synergistic action of lycopene and resveratrol. For the control group, wherein none of the above mentioned phytochemicals are used, the cytotoxic activities were about 10, 20 and 40% at effector/target ratio of 20:1, 50:1 and 100:1, respectively. Upon administration of both lycopene and resveratrol, the NK cytotoxic activities surged to about 20, 40 and 80% at effector/target (E:T) ratio of 25:1, 50:1 and 100:1, respectively.

It is observed from the experimental results as depicted in FIG. 1 that the ability to cause cell lysis increases by approximately two folds upon the introduction of the said pyhtochemicals combination in every experimented E:T ratio. Further, the cytotoxic activities exhibited by said combination is also approximately two times higher than the usage of only lycopene or resveratrol alone. This suggests a synergistic effect wherein both lycopene and resveratrol provides complimentary outcome in boosting the antigen-independent cytotoxicity NK cells in the lymphocytes.

EXAMPLE 2

This experiment attempts to determine the optimal ratio of lycopene to resveratrol to achieve the highest NK cell activation. Five groups of mice (n=6 for each group) were given orally with different ratios of lycopene and resveratrol for 5 days. The mice were killed and the cytotoxicity of NK cells were measured according to the above protocol. The results are tabulated in Table 1 below and a bar graph plotted in FIG. 2.

TABLE 1

Lycopene and resveratrol administrated per day per mouse

|  | Lycopene (mg) | Resveratrol (mg) | Molar ratio of lycopene:resveratrol |
|---|---|---|---|
| Group 1 | 0.7 | 2.8 | 1:10 |
| Group 2 | 1.9 | 1.6 | 1:3 |
| Group 3 | 2.5 | 1 | 1:1 |
| Group 4 | 3.1 | 0.4 | 3:1 |
| Group 5 | 3.35 | 0.15 | 10:1 |

The highest elevation of NK cytotoxicity was achieved at a molar ratio of lycopene:resveratrol=3:1 (7.5:1 in w/w). At this ratio, the percentage of cell lysis is measured to be approximately 63% at an effector/target (E:T) ratio of 50:1.

EXAMPLE 3

Figure 3:
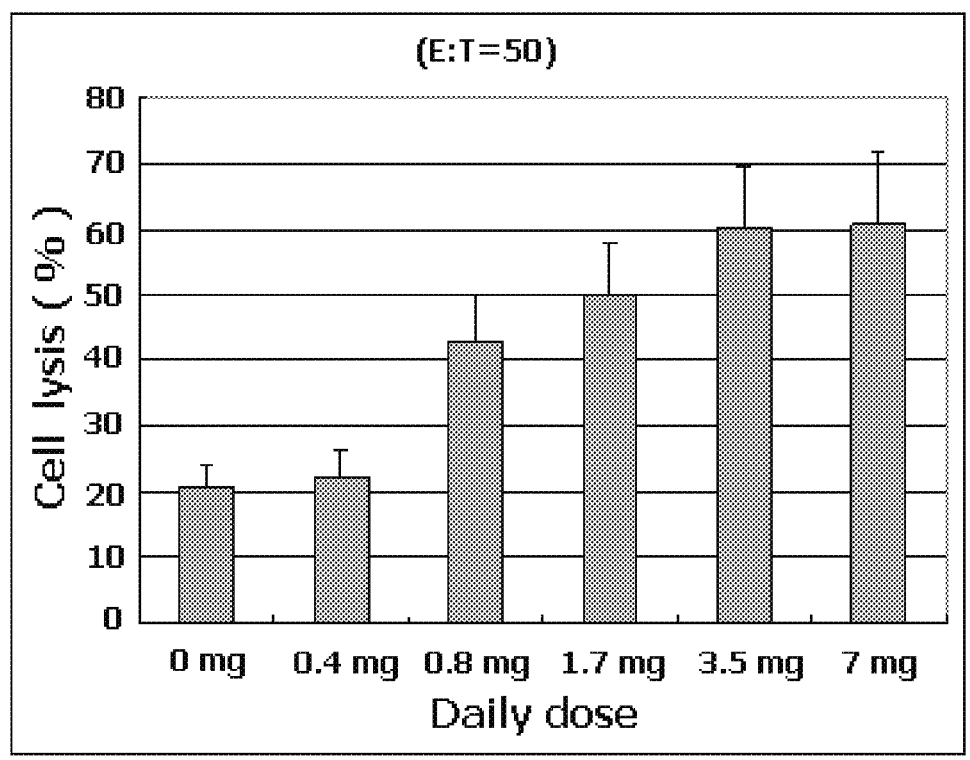
FIG. 3 represents the NK cytotoxicity in mice treated with different doses of the composition of L:R=2.5:1 (w/w).

Dose effect of lycopene:resveratrol on NK cell cytotoxicity. Mice were given different doses of mixture of lycopene and resveratrol (2.5:1 in w/w) daily for 5 days. NK activity at day 5 is investigated and the results plotted in FIG. 3. The cytotoxicities of NK cells were measured at an effector/target ratio of 50:1. The results demonstrated that activation of NK cytotoxity by the mixture is dose-dependent and that the minimum daily dose for the 2.5:1 mixture (w/w) is 3.5 mg for maximal elevation of NK cytotoxicity.

Figure 2:
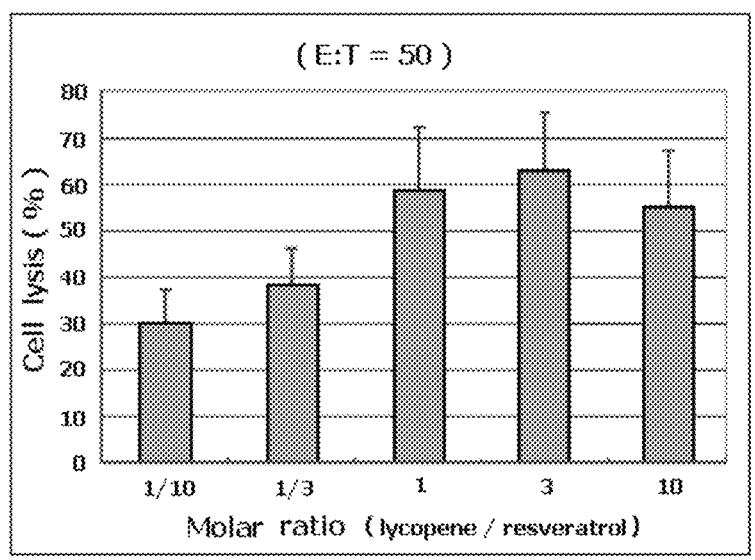
FIG. 2 illustrates a bar graph determining the optimal ratio of lycopene to resveratrol to achieve highest cytotoxic activities of NK cells.
Figure 4:
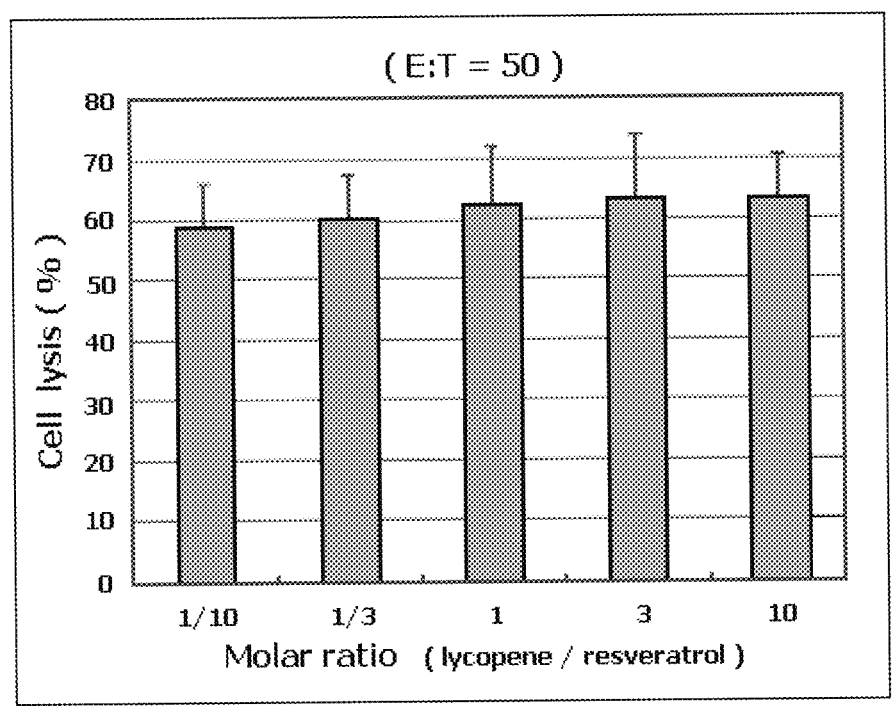
FIG. 4 shows the result of NK cell activity when the doses in FIG. 2 are tripled.

It should be noted that the minimum daily doses to achieve maximal NK cell activity are ratio-dependent. However, when excessive doses are taken in regardless of costs, then maximal activation of NK cells can be achieved in a ratio-independent way. FIG. 4 shows the result of NK cell activity when the dose in FIG. 2 is tripled. It seems that there are minimum doses for each of lycopene and resveratrol to achieve maximal NK cell activity.

EXAMPLE 4

Time-course of NK cell activity-elevation by oral administration of mixture of lycopene and resveratrol (2.5:1 in w/w) is investigated. The mice were orally administrated with 3.5 mg of mixture daily and NK cell cytotoxicity was measured at various days as indicated according the method described in the aforesaid protocol.

Figure 5:
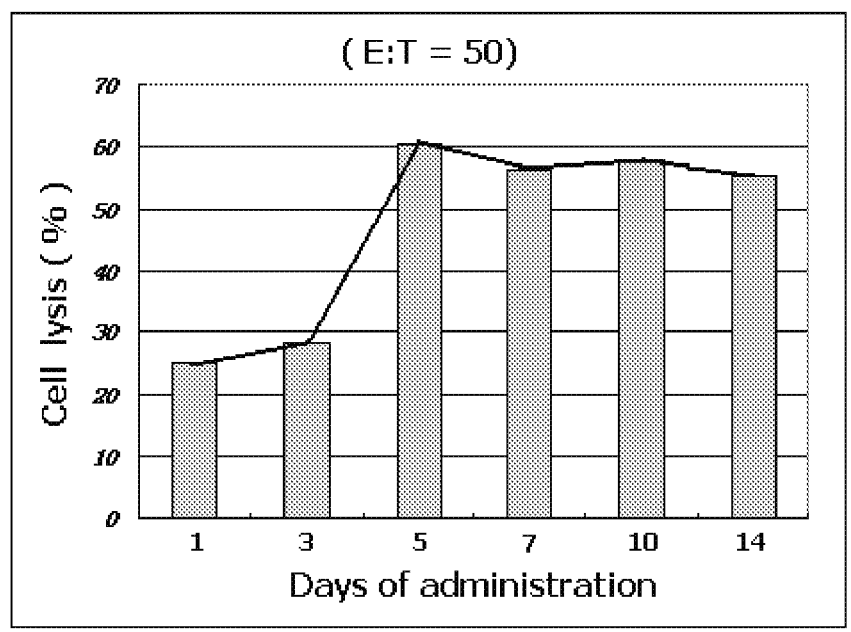
FIG. 5 shows the NK toxicity in mice treated with lycopene at 2.5 mg/day/mouse plus resveratrol at 1 mg/day/mouse over time.

The results are plotted in FIG. 5 which shows that the cytotoxic activity of NK cells began to increase at day 3, and elevated to maximum of about 2.5-fold of that of day 1 at day 5. Elevation of NK cytotoxicity could be sustained as long as the mixture of lycopene and resveratrol is given orally (as shown in the data from day 5 up to day 14 where the trial was not continued.

While it is apparent from the experimental results that a significant synertistic effect may be obtained with the combination of lycopene and resveratrol at the aforesaid specific ratios and length of time of consumption by the subject, it would be apparent to a person skilled in the art to vary the ratios of these 2 phytochemicals according to their respective purity and nano-crytalline form, or according to the richness of their respective raw sources. These ranges and specific ratios may also be subject to change as the phytochemicals are continue to be refined by the industry according to their respective standardized, activated or lyophilized states.

While the above examples show positive results in respect of mice, it is possible to translate the doses from these rodent subjects to humans with established scientific dose translation based on body surface area (BSA) concept where the human dosage may be estimated experientially from statistical data to be in the range of $1/25^{th}$ to $1/50^{th}$ of the dosage for mouse in terms of mg of the active ingredient per kg of body mass, and $1/12^{th}$ the dosage in theory as reported by literature [Ref. 17: Reagan-Shaw (2007)]. From FIG. 3 where the dosage for the mice to achieve maximal activation of NK cells is 3.5 mg/mouse. Since the weight of a mouse is about 20 g, therefore the dosage for mouse can be expressed as 3.5×50=175 mg/kg. Then for a 75 kg human, the dosage based on the aforesaid translation can be calculated as:

experiential value, (75×175)÷(25~50)=262.5~525 mg; and theoretical value, (75×175)÷12=1094 mg.

Based on our aforedescribed product Golden Lypres wherein each of our capsule contains 200 mg of the mixture of lycopene and resveratrol, a dosage of 2-5 capsules per day or 400-1000 mg daily may be prescribed.

EXAMPLE 5

Treatment of Brain Angioma

Figure 6:
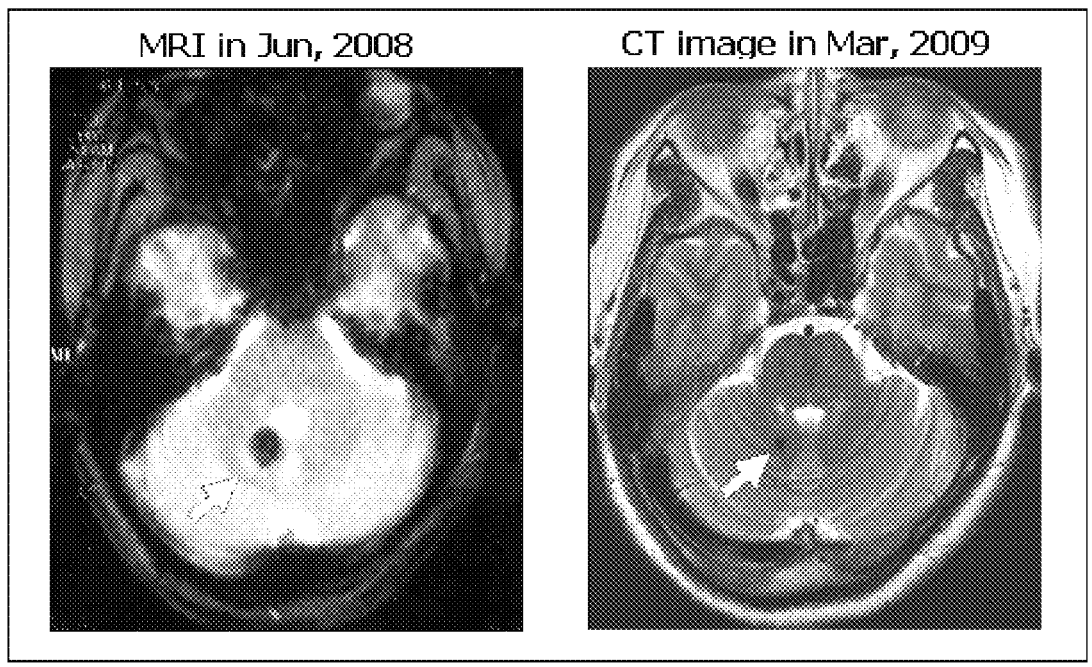
FIG. 6 shows radiographs of a trial subject with brain angioma before and after treatment with a dietary supplement according to one embodiment of our invention.

Case report of a 53-years old female patient. This patient was diagnosed by MRI in August of 2008 to have an angioma about 2 cm in diameter in her brain. She took 4-5 capsules per day of Golden Lypres (each capsule contains 65 mg lycopene and 135 mg of resveratrol, lycopene:resveratrol=1:5 by molar) from October of 2008 to February of 2009. After the disappearance of the symptoms caused by the angioma, she received a CT scan. In FIG. 6, the left side shows the MRI of the patient's brain before taking of Golden Lypres™ (in June 2008, the tumor is indicated by an arrow), and the right shows the CT image after taking of Golden Lypres™ for 4 months (up to February, 2009). FIG. 6 revealed the disappearing of angioma after taking Golden Lypres, and only a small spot remained at the position where angioma was. During this period, the patient did not receive any therapy other than taking Golden Lypres™

EXAMPLE 6

Treatment of Thymus Carcinoma

Figure 7:
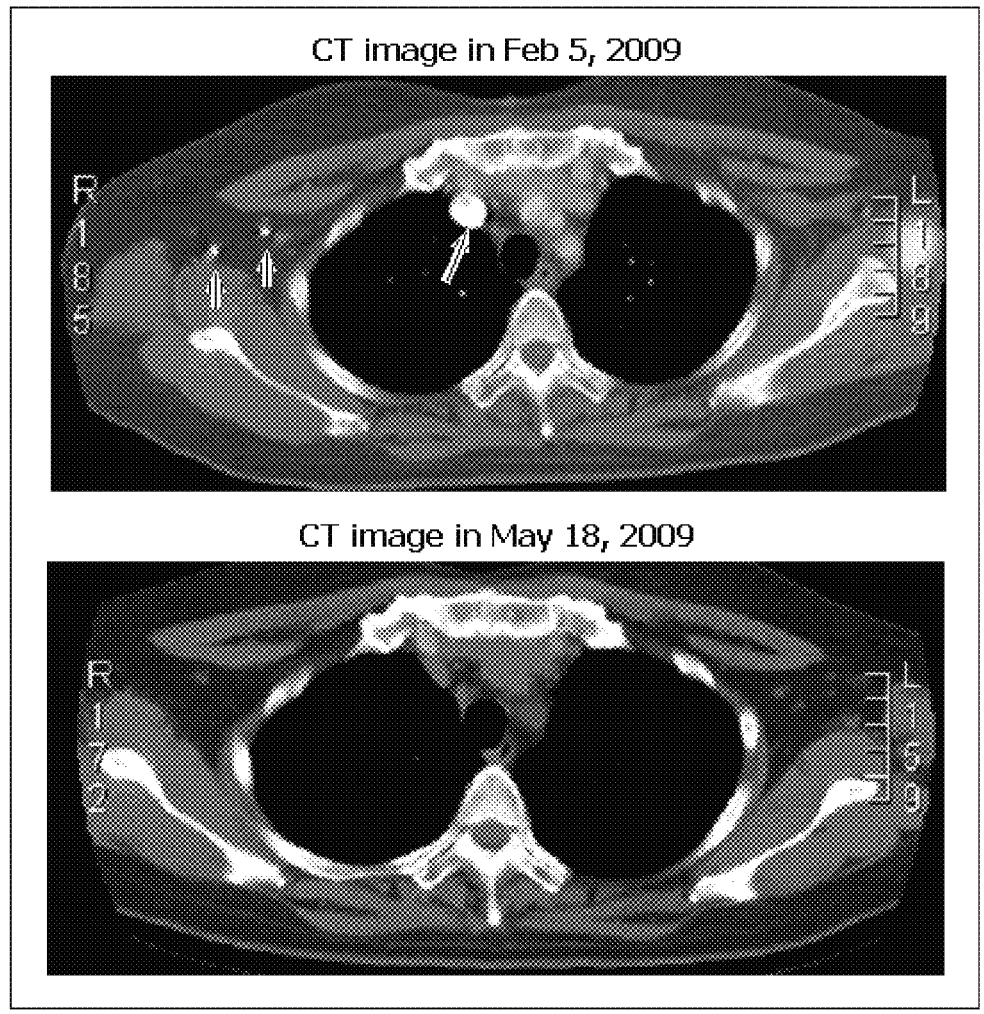
FIG. 7 shows radiographs of another trial subject with thymus carcinoma before and after treatment with a dietary supplement according to one embodiment of our invention.

Case report of a 42-years old female patient. This patient was diagnosed with thymus carcinoma in 2007. She received a series of operation and radiotherapy since then, however, in January of 2009 she was diagnosed to have a relapse of tumor. She began to take 5 capsules per day of Golden Lypres (each capsule contains 65 mg lycopene and 135 mg of resveratrol, lycopene:resveratrol=1:5 by molar) from Feb. 2, 2009. In May 18, 2009, she received another examination by CT, and found that the relapsed tumors disappeared completely. The upper part of FIG. 7 shows the CT image patient's chest before taking Golden Lypres, in which the relapsed tumors are indicated by arrows; and the lower part showes the CT image of same part after taking Golden Lypres for 3.5 months. It is apparent that the tumors in the upper part disappeared completely after taking Golden Lypres. The patient did not take any medication other than Golden Lypres.

EXAMPLE 7

Treatment of a Non-Small Lung Cancer Metastasis in Brain

Figure 8:
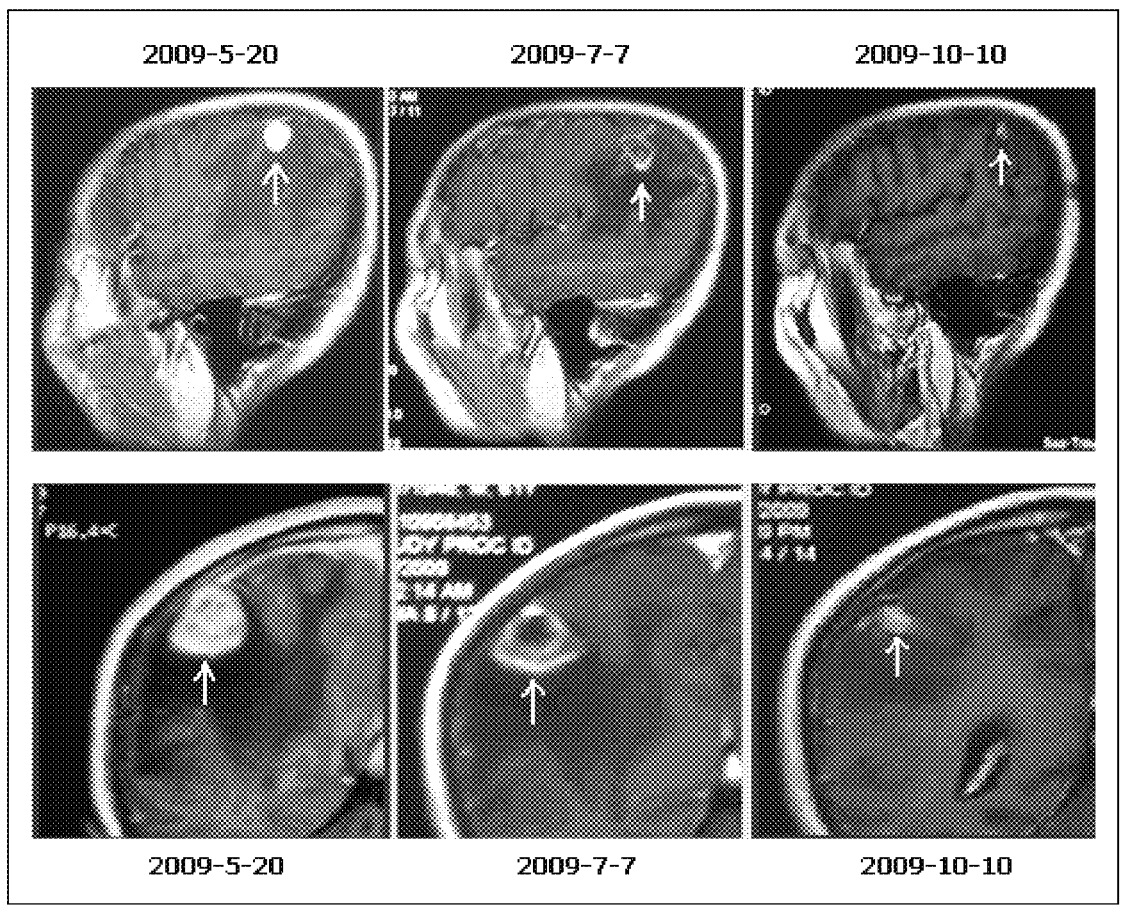
FIG. 8 shows radiographs of yet another trial subject with non-small lung cancer metastasis in brain before and after treatment with a dietary supplement according to one embodiment of our invention.

Case report of a 64-years old male patient. This male patient was diagnosed to have non-small lung cancer at the end of 2007. The tumor was removed by operation and the received chemotherapy after operation. In May of 2009, the patient received a MRI examination for his head because he did not fell well. The result turned out that he had a metastasis in his brain. He began to take 3-4 capsules per day of Golden Lypres (each capsule contains 65 mg lycopene and 135 mg of resveratrol, lycopene:resveratrol=1:5 by molar) from June of 2009. He received two times of CT examination on July 7th, and October 10th, and the results revealed that the tumor was shrinking continuously with time. FIG. 8 shows the size change of the brain metastasis with time. The upper and lower part of FIG. 8 are the different images of the same tumor indicated by arrows.

The aforementioned ratios of lycopene and resveratrol are suggestive based on our results with mice and the respective experimental conditions and may be extrapolated to human body mass and subject to variance or tolerances. Many of the formulation or dosage techniques described above may also be similarly achieved by sequential consumption of the phytochemicals or via other conventional methods known to the notional skilled person. These modifications, adaptations and alternatives are to be considered as equivalents to our invention and fall within the scope and letter of the following claims.

LIST OF NON-PATENT REFERENCES

1. Mein J. R., Lian F., Wang X. D., "Biological activity of lycopene metabolites: Implications for cancer prevention", *Nutr. Rev.* 2008; 66(12):667-83.
2. Giovannucci E., "Tomatoes, tomato-based products, lycopene, and cancer: Review of the epidemiologic literature", *Journal of the National Cancer Institute* 1999; 91: 317-331.
3. Gann P. H., Ma J., Giovannucci E., Willett W., Sacks F. M., Hennekens C. H., Stampfer M. J., "Lower prostate cancer risk in men with elevated plasma lycopene levels: Results of a prospective analysis", *Cancer Res.* 1999 Mar. 15; 59(6):1225-30.
4. Ruhl R., et al. "Carotenoids and their metabolites are naturally occurring activators of gene expression via the pregnane X receptor", *Eur. J. Nutr.* 2004; 43:336-343.
5. Lindshield B. L., et al. "Lycopenoids: are lycopene metabolites bioactive?" *Arch. Biochem. Biophys.* 2007; 458(2):136-40.
6. Mossine V. V., et al. "Interaction of tomato lycopene and ketosamine against rat prostate tumorigenesis" *Cancer Res.* 2008; 68:4384-4391.
7. Venkateswaran V., et al. "A combination of micronutrients is beneficial in reducing the incidence of prostate cancer and increasing survival in the lady transgenic model", *Cancer Prev. Res.* 2009; 2:473-483.
8. Arichi H, et al "Effects of stilbene components of the roots of *Polygonum cuspidatum*" *Chem. Pharm. Bull.* 1982; 30: 1766-1770.
9. Kimura, Y., Okuda, H., and Arichi, S., "Effects of stilbenes, on arachidonate metabolism in leukocytes", *Biochim. Biophys. Acta* 1985; 834: 275-278.
10. Gao X, et al. "Immunomodulatory activity of resveratrol: suppression of lymphocyte proliferation, development of cell-mediated cytotoxicity, and cytokine production", *Biochem. Pharmacol.* 2001; 62: 1299-1308.
11. Tsai S. H., et al. "Suppression of nitric oxide synthase and the down-regulation of the activation of NF-kB in macrophages by resveratrol", *Br. J. Pharmacol.* 1999; 126: 673-680.
12. Falchetti R., et al. "Effects of resveratrol on human immune cell function", *Life Sci.* 2001; 70: 81-96.
13. Heynekamp J. J., et al. "Substituted trans-stilbenes, including analogues of the natural product resveratrol, inhibit the human tumor necrosis factor alpha-induced activation of transcription factor nuclear factor KappaB", *J. Med. Chem.* 2006; 49: 7182-7189.
14. Andlauer W, et al. "Assessment of resveratrol bioavailability in the perfused small intestine of the rat", *Drugs Exp. Clin. Res.* 2000; 26: 47-55.
15. De Santi, C. et al. "Sulphation of resveratrol, a natural product present in grapes and wine, in the human liver and duodenum", *Xenobiotica*, 2000; 30: 609-17.
16. Vitrac X., et al. "Distribution of 14C-trans-resveratrol, a cancer chemopreventive polyphenol, in mouse tissues after oral administration", *Life Sci.* 2003; 72: 2219-2233.
17. Shannon Reagan-Shaw, et al., "Dose translation from animal to human studies revisited, *The FASEB Journal*, 2007; 22: 659-661.
18. Zhang H, & Huang W. "Fusion proteins of Hsp70 with tumor-associated antigen acting as a potent tumor vaccine and the C-terminal peptide-binding domain of Hsp70 being essential in inducing antigen-independent anti-tumor response in vivo" *Cell Stress & Chaperones*, 2006; 11(3): 216-226.

What is claimed is:

1. A composition comprising a carotenoid and a terpenoid wherein the composition comprises at least a carotenoid and at least a terpenoid in a therapeutically effective amount for metabolically elevating activity of a large granular lymphocyte (LGL) and a natural killer (NK) cells,
and the carotenoid comprises a lycopene and the terpenoid comprises a resveratrol in a molar ratio of between about 1:3 to 3:1, and
wherein the elevated NK cell activity includes increased proportion of NK cells among total lymphocytes.

2. The composition of claim 1, wherein the elevated NK cell activity includes providing biochemical signal triggering NK cells into cytotoxic or cytolytic response.

3. The composition of claim 1, wherein the elevated NK cell activity includes increasing the response potential of individual NK cells.

4. The composition of claim 2, wherein the biochemical signal triggering includes any one or combination of double-stranded RNA, cytokines, Fc receptor and other applicable ligand receptors.

5. The composition of claim 1, wherein the elevated NK cell activity includes prolonged cytotoxicity.

6. The composition of claim 1, wherein the ratio of lycopene:resveratrol is about 1:3 by molar.

7. The composition of claim 1, wherein the ratio is between about 1:1 to 3:1 by molar.

8. The composition of claim 1, formulated as a pharmaceutical, a capsule, a dietary supplement or a food product.

9. The composition of claim 8, formulated to provide a therapeutically effective amount to a mammal.

10. The composition of claim 9, provided in a dosage of between about 3.5 mg per day per 20 g of a mammalian body mass.

11. The composition of claim 8, provided in a dosage of between about 400 mg to 1000 mg per day.

12. The composition of claim 8, formulated for oral intake.

13. The composition of claim 8, formulated with each of said lycopene and resveratrol being delivered or provided for intake sequentially.

14. A method for triggering NK cells into cytotoxic or cytolytic response comprising:
(a) providing a lycopene and a resveratrol according to claim 1,
(b) administering the lycopene and a resveratrol of (a) to a patient in need thereof, thereby triggering NK cells into a cytotoxic or a cytolytic response.

15. The method of claim 14, wherein said lycopene and resveratrol is consumed in a single preparation containing both.

16. The composition of claim 1, wherein the ratio is at 3:1 by molar.

17. The method of claim 14, wherein said lycopene and resveratrol are consumed in as a single preparation containing both.

18. The method of claim 14, wherein said lycopene and resveratrol are consumed simultaneously, and consumed in a preparation for each of said lycopene and resveratrol formulated for simultaneous consumption.

19. The method of claim 14, wherein said lycopene and resveratrol are consumed sequentially in same or reverse order, and are formulated or prepared for consumption sequentially in same or reverse order.

* * * * *